(12) United States Patent
Sardar et al.

(10) Patent No.: US 9,173,562 B2
(45) Date of Patent: Nov. 3, 2015

(54) METHOD AND APPARATUS FOR DIAGNOSING NEOVASCULARIZED TISSUES

(75) Inventors: Dhiraj Sardar, San Antonio, TX (US); Andrew T. C. Tsin, Fair Oaks Ranch, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1956 days.

(21) Appl. No.: 10/543,001

(22) PCT Filed: Jan. 23, 2004

(86) PCT No.: PCT/US2004/001836
§ 371 (c)(1),
(2), (4) Date: May 23, 2006

(87) PCT Pub. No.: WO2004/064615
PCT Pub. Date: Aug. 5, 2004

(65) Prior Publication Data
US 2006/0293599 A1 Dec. 28, 2006

Related U.S. Application Data

(60) Provisional application No. 60/442,135, filed on Jan. 23, 2003.

(51) Int. Cl.
*A61B 6/00* (2006.01)
*A61B 3/12* (2006.01)
*A61B 5/00* (2006.01)

(52) U.S. Cl.
CPC ............. *A61B 3/1225* (2013.01); *A61B 5/0059* (2013.01)

(58) Field of Classification Search
USPC ........................... 600/452, 489, 402; 351/205
See application file for complete search history.

(56) References Cited

U.S. PATENT DOCUMENTS

| | | | | |
|---|---|---|---|---|
| 5,002,384 A | * | 3/1991 | Trachtman | 351/203 |
| 5,303,709 A | * | 4/1994 | Dreher et al. | 600/476 |
| 5,568,208 A | * | 10/1996 | Van de Velde | 351/221 |
| 5,632,282 A | * | 5/1997 | Hay et al. | 600/558 |
| 5,670,151 A | * | 9/1997 | Larrick et al. | 424/183.1 |

(Continued)

OTHER PUBLICATIONS

Anderson and Paris, "The optics of human skin," *J. Invest. Dermatol.*, 77:13-19, 1981.

(Continued)

*Primary Examiner* — Joel F Brutus
(74) *Attorney, Agent, or Firm* — Norton Rose Fulbright US LLP

(57) ABSTRACT

Disclosed is a method for detecting neovascularized tissue that includes placing a tissue in the path of a light beam, measuring a polarization shift of the light beam, and detecting neovascularized tissue if the measured polarization shift corresponds to a polarization shift of a neovascularized tissue. Also disclosed is an apparatus for detecting neovascularized tissue that includes a laser, a polarizer coupled to the laser, a tissue sample holder coupled to the polarizer, an analyzer coupled to the tissue sample holder, a detector coupled to the analyzer, and a data acquisition system coupled to the detector, wherein the data acquisition system is configured to measure a polarization shift of a light beam emitted by the laser and diagnose an ocular disease if the measured polarization shift corresponds to a polarization shift of a neovascularized tissue.

37 Claims, 5 Drawing Sheets

(56) References Cited

U.S. PATENT DOCUMENTS

| | | | |
|---|---|---|---|
| 5,767,079 A * | 6/1998 | Glaser et al. | 514/12 |
| 6,112,114 A | 8/2000 | Dreher | 600/476 |
| 6,179,421 B1 * | 1/2001 | Pang | 351/205 |
| 6,276,798 B1 | 8/2001 | Gil et al. | 351/206 |
| 6,293,674 B1 | 9/2001 | Huang et al. | 351/221 |
| 6,356,036 B1 | 3/2002 | Zhou | 315/215 |
| 6,404,497 B1 | 6/2002 | Backman et al. | 356/369 |
| 6,419,361 B2 | 7/2002 | Cabib et al. | 351/221 |
| 2001/0033364 A1 | 10/2001 | Cabib et al. | 351/221 |
| 2002/0097376 A1 | 7/2002 | Applegate et al. | 351/205 |
| 2002/0101566 A1 | 8/2002 | Elsner et al. | 351/200 |
| 2006/0258629 A1 * | 11/2006 | Freeman | 514/150 |

OTHER PUBLICATIONS

Beek et al., "In vitro double-integrating-sphere optical properties of tissues between 630 and 1064 nm," *Phys. Med. Biol.*, 42:2255-2261, 1997.

Boettner and Wolter, "Transmission of the ocular media," *Invest. Ophthalmol.*, 1:776-783, 1962.

Campochiaro, "Retinal and choroidal neovascularization," *J. Cell. Physiol.*, 184:301-310, 2000.

Chandrasekhar, In: *Radiative Transfer.*, Dover, New York, pp. 1-53, 1960.

Delori and Pflibsen, "Spectral reflectance of the human ocular fundus," *Appl. Opt.*, 28(6):1061-1077, 1989.

Dryja et al., "Elemental analysis of melanins from bovine hair, iris, choroid, and retinal pigment epithelium." *Invest. Ophthalmol. Visual Sci.*, 18:231-236, 1979.

Ducros et al., "Primate retina imaging with polarization-sensitive optical coherence tomography," *J. Opt. Soc. Am. A*, 18:2945-2956, 2001.

Ertefai and Profio, "Spectral transmittance and contrast in breast diaphanography," *Med. Phys.*, 12:393-400, 1985.

Flower et al., "The effect of blood on ocular fundus reflectance and determination of some optical properties of retinal blood vessels," *Invest. Ophthalmol. Visual Sci.*, 17(6):562-565, 1978.

Geerates and Berry, "Ocular spectral characteristics as related to hazards from lasers and other light sources," *Amer. J. Ophthalmol.*, 66:15-20, 1968.

Groenhuis et al., "Scattering and absorption of turbid materials determined from reflection measurements. 1: Theory," *Appl. Opt.*, 22:2456-2462, 1983.

Hecht, "Table of Contents," In: *Optics*, 4$^{th}$ ed., Addison Wesley, New York, 2002.

Ishimaru, "Table of Contents," In: *Wave propagation and scattering in random media*, vol. 1, Academic Press, New York, 1978.

Kahn and Hiller, "Blindness caused by diabetic retinopathy," *Am. J. Ophthalmol.*, 78:58-67, 1974.

Klein and Klein, "Table of Contents," In: *Group NDD, Ed. Diabetes in America.* Washington, D.C.: National Institute of Health, 294, 1995.

Knighton et al., "The Spectral Reflectance of the Nerve Fiber Layer of the Macaque Retina," *Invest. Ophthalmol. Visual Sci.*, 30(11):2393-2402, 1989.

Kottler, "Turbid Media with Plane-Parallel Surfaces," *J. Opt. Soc. Am.*, 50:483-490, 1960.

Kubelka, "New Contributions of the Optics of Intensely Light-Scattering Materials. Part I," *J. Opt. Soc. Am.*, 38:448-457, 1948.

Maher, In: *Transmission and absorption coefficients for ocular media of the rhesus monkey*, USAF School of Aerospace Med., Brooks AF Base, TX, Report SAM-TR-78-32, pp. 1-40, 1978.

McLeod et al., "Vasoproliferation in the neonatal dog model of oxygen-induced retinopathy," *Invest. Ophthalmol. Visual Sci.*, 37:1322-1333, 1996.

McLeod et al., "Visualization of a developing vasculature," *Microvasc. Res.*, 33:257-269, 1987.

Mourant et al., "Scattering properties of biological cells," *OSA TOPS*, 22:11-14, 1998.

PCT International Search Report and Written Opinion, issued in International Application No. PCT/US04/01836, dated Nov. 18, 2004.

Prahl et al., "A Monte Carlo Model of Light Propagation in Tissue," *SPIE Institute Series*, 5:102-111, 1989.

Prahl et al., "Determining the optical properties of turbid media by using the adding-doubling method," *Appl. Opt.*, 32:559-568, 1993.

Prince et al., "Preferential Light Absorption in Atheromas in Vitro: Implications for Laser Angioplasty," *J. Clin. Invest.*, 78:295-302, 1978.

Reynolds et al., "Diffuse reflectance from a finite blood medium: applications to the modeling of fiber optic catheters," *Appl. Opt.*, 15:2059-2067, 1978.

Sardar and Levy, "Optical Properties of Whole Blood," *Lasers Med. Sci.*, 13:106-111, 1998.

Sardar et al., "Optical characterization of melanin," *J. Biomed. Opt.*, 6:404-411, 2001.

Sarna, "Properties and function of the ocular melanin—a photobiophysical view," *J. Photochem. Photobiol.*, 12(3):215-258, 1992.

van den Berg and Spekreijse, "Near infrared light absorption in the human eye media," *Vision Res.*, 37:249-253, 1997.

Van Gemert and Star, "Relations Between the Kubelka-Munk and the Transport Equation Models for Anisotropic Scattering," *Lasers Life Sci.*, 1:287-298, 1987.

Van Gemert et al., "Optical properties of human blood vessel wall and plaque," *Lasers Surg. Med.*, 5:235-237, 1985.

Van Gemert et al., "Tissue Optics for a Slab Geometry in the Diffusion Approximation," *Lasers Med. Sci.*, 2:295-302, 1987.

Vos et al., "Absolute Spectral Reflectance of the Fundus Oculi," *J. Opt. Soc. Am.*, 55:573-574, 1965.

Wan et al., "Analytical Modeling for the Optical Properties of the Skin with In Vitro and In Vivo Applications," *Photochem. Photobiol.*, 34:493-499, 1981.

* cited by examiner

METHOD AND APPARATUS FOR DIAGNOSING NEOVASCULARIZED TISSUES

This application is a national phase application under 35 U.S.C. §371 of International Application No. PCT/US2004/001836, filed 23 Jan. 2004, which claims priority to U.S. Provisional Application No. 60/442,135, filed 23 Jan. 2003. The entire text of each of the above-referenced disclosures is specifically incorporated herein by reference without disclaimer.

STATEMENT AS TO RIGHTS TO INVENTIONS MADE UNDER FEDERALLY-SPONSORED RESEARCH AND DEVELOPMENT

This invention was made with support from the National Science Foundation and the National Institutes of Health. The Government may have certain rights in this invention.

BACKGROUND OF THE INVENTION

1. Field of the Invention

The invention relates generally to the field of medical diagnostics. More particularly, the invention relates to the diagnosing of neovascularized tissue.

2. Discussion of the Related Art

In recent years, there has been a considerable interest in the investigation of ocular neovascularization. Ocular neovascularization is the formation of new blood vessels in the development of diseases such as, for example, macular degeneration and diabetic retinopathy.

Retinal neovascularization resulting from diabetic retinopathy is the most common cause of blindness in young patients in major industrialized countries, and choroidal neovascularization resulting from age-related macular degeneration is the most common cause of severe vision loss in elderly patients.

During neovascularization, increased amounts of blood in capillaries change the optical properties of the tissue. Meanwhile, it has been known that ocular tissues are inherently birefringent and may alter the polarization of incident light in scattering events according to the their geometry and optical properties.

What is needed is a noninvasive method and apparatus for detecting neovascularized ocular tissues. What is also needed is a noninvasive method and apparatus for diagnosing ocular diseases such as diabetic retinopathy and macular degeneration.

SUMMARY OF THE INVENTION

There is a need for the following embodiments. Of course, the invention is not limited to these embodiments.

According to an aspect of the invention, a method for diagnosing an ocular disease includes placing an ocular tissue in the path of a light beam, measuring a polarization shift of the light beam, and diagnosing an ocular disease if the measured polarization shift corresponds to a polarization shift of a neovascularized tissue.

According to another aspect of the invention, an apparatus for diagnosing an ocular disease includes: a laser, a polarizer coupled to the laser, a tissue sample holder coupled to the polarizer, an analyzer coupled to the tissue sample holder, a detector coupled to the analyzer, and a data acquisition system coupled to the detector, the data acquisition system configured to measure a polarization shift of a light beam emitted by the laser and diagnose an ocular disease if the measured polarization shift corresponds to a polarization shift of a neovascularized tissue.

According to yet another aspect of the invention, a method for detecting neovascularized tissue, includes placing a tissue in the path of a light beam, measuring a polarization shift of the light beam, and detecting neovascularized tissue if the measured polarization shift corresponds to a polarization shift of a neovascularized tissue.

According to a fourth aspect of the invention, an apparatus for detecting neovascularized tissue, includes: a laser, a polarizer coupled to the laser, a tissue sample holder coupled to the polarizer, an analyzer coupled to the tissue sample holder, a detector coupled to the analyzer, and a data acquisition system coupled to the detector, the data acquisition system configured to measure an intensity of a light beam emitted by the laser and diagnose an ocular disease if the measured intensity corresponds to an intensity of a neovascularized tissue.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting, embodiments illustrated in the drawings, wherein like reference numerals (if they occur in more than one view) designate the same or similar elements. The invention may be better understood by reference to one or more of these drawings in combination with the description presented herein. It should be noted that the features illustrated in the drawings are not necessarily drawn to scale.

DESCRIPTION OF ILLUSTRATIVE EMBODIMENTS

The invention and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating illustrative embodiments of the invention, are given by way of illustration only and not by way of limitation. Various substitutions, modifications, additions and/or rearrangements within the spirit and/or scope of the underlying inventive concept will become apparent to one of ordinary skill in the art from this disclosure.

The invention may include a method and/or apparatus for determining an optical property of an ocular tissue. The invention may also include a method and/or apparatus for detecting neovascularized ocular tissues and diagnosing medical conditions or diseases. Examples of ocular neovascularized tissue may include but are not limited to: diabetic retinal tissue, choroidal capillaries, and tumor tissues.

The invention may include a method for relating the optical properties of a biological tissue to its constituents. During neovascularization, increased amounts of blood in capillaries may change the optical properties of the tissue. For example, retinal vascular development may occur due to a combination of vasculogenesis and angiogenesis. Retinal and retinal pigment epithelium (RPE)/choroidal vessels may multiply with increased amounts of blood in the capillaries, thereby enhancing their scattering, intensity change, and polarization shift properties.

In one embodiment, the invention may include using a probing light or laser which may be linearly polarized at various angles, such as, for example: right circularly, left circularly, or elliptically polarized. Light reflected from (or transmitted through) the tissue may be analyzed. An analytical method may be used to characterize the optical properties of the tissue, such as the one demonstrated by the Stokes-vector Mueller-matrix approach to polarization and light scattering.

The invention may include a noninvasive method and/or apparatus for the early detection and diagnosis of ocular diseases associated with neovascularization processes, such as diabetic retinopathy and macular degeneration. According to one aspect of the invention, neovascularized ocular tissues may exhibit significantly different optical properties (such as higher scattering and increased degree of polarization shifts of the backscattered polarized light) than healthy tissues. According to another aspect of the invention, these differences may be quantitatively accessed at different pathological stages using tissue polarimetry.

Figure 1:
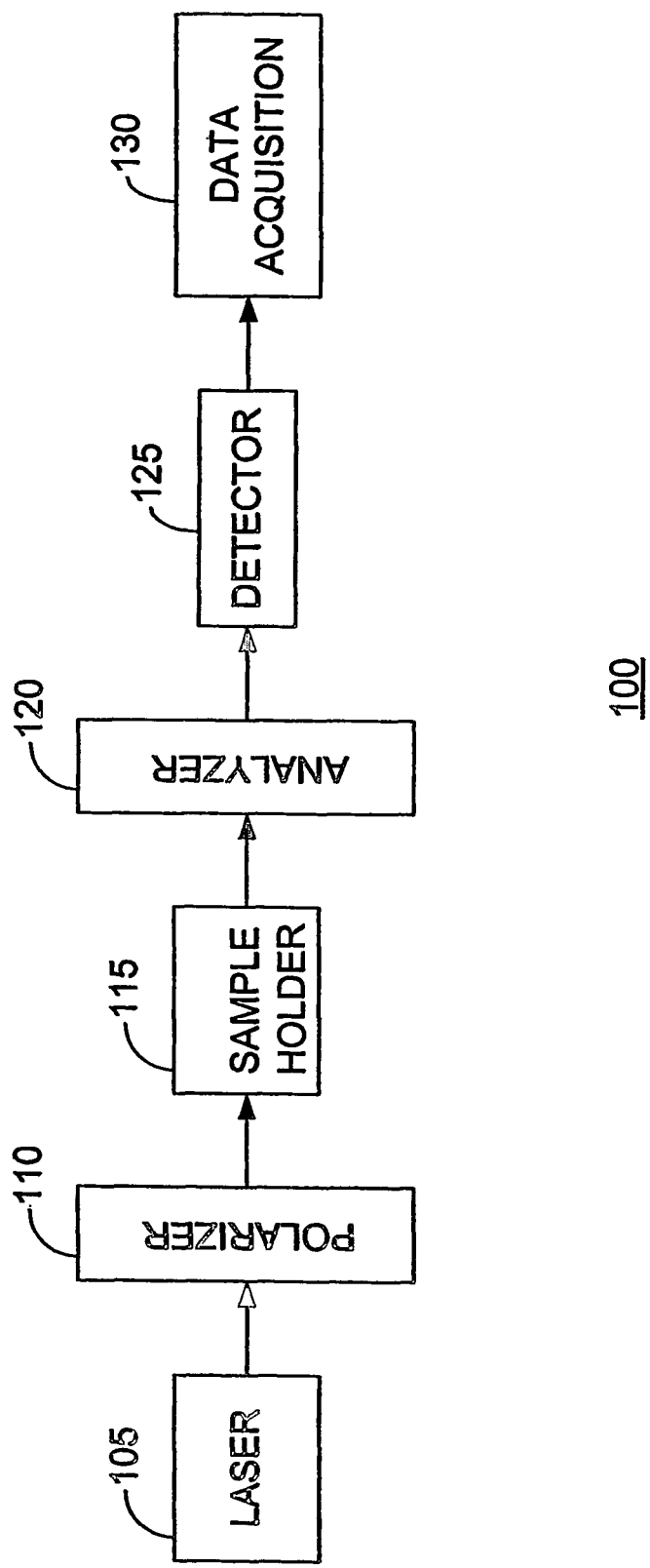
FIG. 1 is a diagram of a setup for polarization measurements of a retinal tissue, representing an embodiment of the invention.

Referring to FIG. 1, a diagram of a setup 100 for polarization measurements for a retinal tissue is depicted, according to one embodiment of the invention. A laser 105 is coupled to a first polarizer 110. The first polarizer 110 is coupled to a sample holder 115 comprising retinal tissue. The sample holder 115 is coupled to a second polarizer/analyzer 120. The analyzer 120 is coupled to a detector 125. The detector 125 is coupled to a data acquisition system 130. The laser 105, the detector 125, and the data acquisition system 130 may each be coupled to a power supply (not shown).

In one embodiment, the laser 105 may be a He—Ne laser (such as the 1101P laser by Uniphase Corporation) with a power of 4 milliwatt and beam diameter of 3 mm. The laser 105 creates a laser beam that is passed through the linear polarizer 110, the retinal tissue in the sample holder 115, and the analyzer 120. The polarizers/analyzers 110, 120 may be, for example, the 25010 polarizers from Oriel Corporation. The detector 125 may be a photodiode detector which is coupled to a power supply such as, for example, a Cenco model 31382 supply (not shown). The detector 125 is connected to the data acquisition system 130, which may be, for example, a Fluke model 77 series II multimeter. The data acquisition system 130 may be a meter, a digital meter, a data aqcuisition system, a computer, or the like. The data acquisition system 130 may measure, for example, a polarization shift and/or an intensity.

In a first step of a data acquisition operation, the sample holder 115 and the analyzer 120 are absent from the setup 100, and the polarizer 110 is rotated until the maximum beam intensity is obtained, indicating that the beam is completely polarized. Once the maximum laser intensity is achieved, the analyzer 120 may be placed between the detector 125 and the polarizer 110 (still without the sample holder 115 in the light path). The analyzer 120 is rotated to maximize the light intensity so that that the transmission axes of the polarizer 110 and the analyzer 120 are parallel with respect to each other. Next, the sample holder 115 containing a retinal tissue may be placed between the polarizer 110 and the analyzer 120, causing the polarization plane to shift due to the anisotropic property of the tissues. The polarization shift of the scattered laser light may be observed and the shift may be determined by rotating the analyzer 120 until maximum light intensity is measured with the data acquisition system 130. The data acquisition system 130 may take laser polarization and/or laser intensity measurements corresponding to different locations on the retinal tissue and process the acquired data. In one embodiment, an average of three measurements is taken for each sample location.

Due to the opacity of RPE/choroidal tissue, laser beams may not be able to penetrate RPE/choroidal tissue samples. In one embodiment, a modification of the experimental setup 100 detailed in FIG. 1 may be made for measurements of the polarized light scattered off a RPE/choroidal tissue sample.

Figure 2:
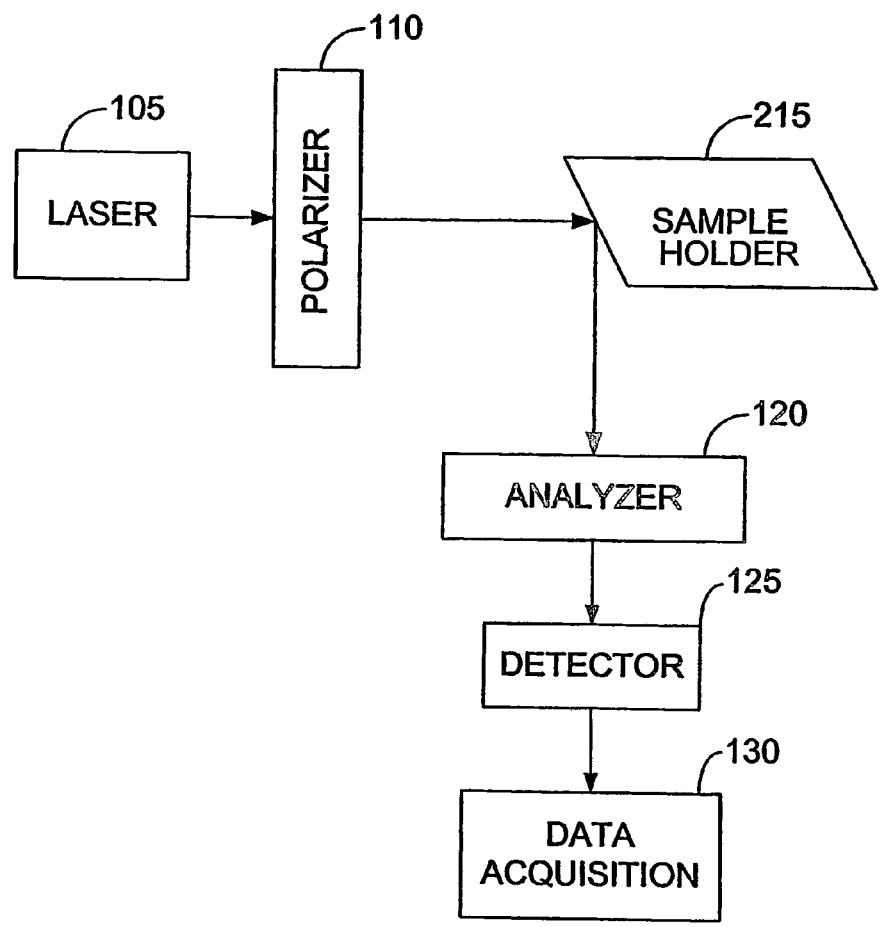
FIG. 2 is a diagram of a setup for polarization measurements of a retinal pigment epithelium (RPE)/choroidal tissue, representing an embodiment of the invention.

Referring to FIG. 2, a diagram of an experimental setup 200 for polarization measurements of a RPE/choroidal tissue is depicted, according to one embodiment of the invention. A clean glass slide (not shown) may be placed in the sample holder 215, and the scattered beam may be directed at approximately a right angle with respect to the direction of the incident laser beam. The analyzer 120 and the detector 125 may be aligned with the direction of the most intense scattered beam, and the same technique as described above may be employed to assure that the transmission axes of both the polarizer 110 and the analyzer 120 are perpendicular with respect to each other. The glass slide may then be replaced by the RPE/choroidal tissue. The polarization shift for the RPE/choroid tissue may be determined in the same manner as retinal tissue of FIG. 1. The data acquisition system 130 may take laser polarization and/or laser intensity measurements corresponding to different locations on the RPE/choroid tissue and process the acquired data. In one embodiment, an average of three measurements is taken for each sample location.

The invention may include using an experimental methodology as described above for performing polarization measurements on retinal and RPE/choroidal tissues placed together (combination retinal and RPE/choroidal tissues). In this case, a retinal tissue sample may be placed in front of the RPE/choroidal tissue sample.

EXAMPLES

Specific embodiments of the invention will now be further described by the following nonlimiting examples which will serve to illustrate in some detail various features. The following examples are included to facilitate an understanding of ways in which the invention may be practiced. It should be appreciated that the examples which follow represent embodiments discovered to function well in the practice of the invention, and thus can be considered to constitute preferred modes for the practice of the invention. However, it should be appreciated that many changes can be made in the exemplary embodiments which are disclosed while still obtaining like or similar results without departing from the spirit and scope of the invention. Accordingly, the examples should not be construed as limiting the scope of the invention.

Example 1

Samples of bovine ocular (retina and RPE/choroid) tissues were prepared from fresh eyes obtained from a slaughter plant and preserved at 0° C. during transportation for 45 min. Upon arrival in the laboratory, anterior segments including cornea, lense, and aqueous vitreous humor fluid were removed from the eyes. Next, the retina was carefully lifted from the posterior eye cup and mounted between two glass slides. The RPE/choroid was subsequently removed from the eye and similarly mounted. The thickness of the retinal and RPE/choroidal tissues were approximately 0.15 and 0.10 mm, respectively. A small amount of vacuum grease was applied to the edges of the glass slides in order to maintain the moisture of the sample. All data was collected at room temperature within two hours from the slaughter of the animals.

The data acquisition operation described herein was performed, and polarization shift measurements of both the retinal and RPE/choroidal tissues taken from the bovine left and right eyes are given in Table I.

TABLE I

Polarization shift (in degrees) in the bovine retinal and RPE/choroidal tissues

| Trial Number | Retina | | RPE/Choroid | |
|---|---|---|---|---|
| | Left Eye | Right Eye | Left Eye | Right Eye |
| 1 | 5.96 | 6.96 | 10.92 | — |
| 2 | 5.92 | 4.92 | 10.00 | 11.94 |
| 3 | 6.94 | 5.00 | 11.96 | 13.92 |
| Average | 6.27 | 5.63 | 10.96 | 8.62 |

Polarization shift measurements of combination retinal and RPE/choroidal tissues taken from the bovine left and right eyes are given in Table II.

TABLE II

Polarization shift (in degrees) for the combination of retinal and RPE/choroidal tissues

| Trial Number | Retina & RPE/Choroid | |
|---|---|---|
| | Left Eye | Right Eye |
| 1 | 11.92 | 15.92 |
| 2 | 11.2 | 14.94 |
| 3 | 13.96 | 16.92 |
| Average | 12.36 | 15.93 |

Variations in the polarization shifts between the left and right eyes may be due to minuscule thickness differences in the prepared tissue samples, particularly, when different locations were chosen for collecting the data. The data from tables I and II suggest that the bovine ocular tissues are polarization dependent, and that the RPE/choroidal tissue shows a higher degree of polarization shift than the retina.

Polarization shifts in the bovine retina have also been measured at 24 hours of interval. During this period of time, the sample was kept refrigerated. It was found that the polarization shift decreases significantly after 48 hours after the sample preparation as shown in Table III below. A decrease in polarization shift may be attributed to the physiological degradation of the retinal tissue, thereby changing the its optical properties.

TABLE III

Polarization shift (in degrees) of bovine retinal tissue over time

| Time(hrs) | Polarization Shift |
|---|---|
| 0 | 6.96 |
| 24 | 5.92 |
| 48 | 2.10 |

Example 2

Retinal and RPE/choroidal tissues from human healthy and diseased eyes (obtained from the National Disease Research Interchange) were carefully dissected and individually placed between a pair of glass slides separated by two cover slips or spacers at the two ends of the glass slides. Spacers may be used to prevent the glass slides from squeezing the tissues from its original, native shape to a compressed form. A small amount of vacuum grease was used in order to seal the open space between the glass slides so that the tissue was kept moist and retained in the space between the glass slides. These precautions may be taken in order to maintain the integrity of tissues' physiological properties, and also to make sure that the tissue optical properties do not change due to the compression and/or dehydration of the samples.

The data acquisition operation described herein was performed, and the polarization shift ($\Delta\theta$) and intensity measurements for healthy human retinal, RPE/choroidal, and combination retinal and RPE/choroidal tissues are shown in Table IV.

TABLE IV

Polarization shift (Δθ) and intensity for healthy human ocular tissue

| Eye | Trial Number | Retina Δθ | Retina Intensity (mV) | RPE/Choroid Δθ | RPE/Choroid Intensity (mV) | Retina & RPE/Choroid Δθ | Retina & RPE/Choroid Intensity (mV) |
|---|---|---|---|---|---|---|---|
| Left | 1 | 3.50 | 298.10 | 8.00 | 313.10 | 8.50 | 313.20 |
|  | 2 | 3.00 | 308.60 | 6.50 | 322.50 | 7.50 | 312.40 |
|  | 3 | 2.00 | 315.00 | 5.00 | 333.60 | 6.00 | 282.60 |
|  | AVG | 2.83 | 307.23 | 6.5 | 323.07 | 7.33 | 302.73 |
| Right | 1 | 3.00 | 313.50 | 7.50 | 322.10 | 8.00 | 306.70 |
|  | 2 | 2.80 | 310.20 | 6.50 | 266.40 | 6.50 | 319.10 |
|  | 3 | 1.50 | 315.80 | 4.90 | 304.30 | 6.00 | 326.30 |
|  | AVG | 2.43 | 313.17 | 6.30 | 297.60 | 6.83 | 317.37 |

The polarization shift (Δθ) and intensity measurements for diseased human retinal, RPE/choroidal, and combination retinal and RPE/choroidal tissues is shown in Table V.

TABLE V

Polarization shift (Δθ) and intensity for diseased human ocular tissue

| Eye | Trial Number | Retina Δθ | Retina Intensity (mV) | RPE/Choroid Δθ | RPE/Choroid Intensity (mV) | Retina & RPE/Choroid Δθ | Retina & RPE/Choroid Intensity (mV) |
|---|---|---|---|---|---|---|---|
| Left | 1 | 6.50 | 2.61.90 | 11.00 | 259.25 | 12.50 | 210.70 |
|  | 2 | 6.00 | 269.75 | 10.00 | 239.40 | 9.75 | 205.90 |
|  | 3 | 5.00 | 289.50 | 8.50 | 218.70 | 7.50 | 201.50 |
|  | AVG | 5.83 | 273.72 | 9.88 | 239.12 | 9.92 | 272.37 |
| Right | 1 | 6.50 | 227.25 | 10.00 | 249.10 | 10.00 | 230.10 |
|  | 2 | 6.00 | 255.70 | 9.50 | 218.40 | 9.50 | 219.20 |
|  | 3 | 4.9 | 301.80 | 8.50 | 208.90 | 7.50 | 208.90 |
|  | AVG | 5.8 | 261.58 | 9.33 | 225.47 | 9.00 | 219.40 |

A comparison between the average polarization shifts (Δθ) and average intensities between the diseased and healthy retinal, RPE/choroidal, and retinal and RPE/choroidal tissues (in stack) from the human left and right eyes is shown in table VI.

TABLE VI

Comparison between healthy and diseased human ocular tissue

| Condition | Eye | Retina Δθ | Retina Intensity (mV) | RPE/Choroid Δθ | RPE/Choroid Intensity (I) (mV) | Retina & RPE/Choroid Δθ | Retina & RPE/Choroid Intensity (I) (mV) |
|---|---|---|---|---|---|---|---|
| Healthy | Left | 2.83 | 307.23 | 6.50 | 323.07 | 7.33 | 302.73 |
|  | Right | 2.43 | 313.17 | 6.30 | 297.60 | 6.83 | 317.37 |
| Diseased | Left | 5.83 | 273.72 | 9.88 | 239.12 | 9.92 | 272.37 |
|  | Right | 5.8 | 261.58 | 9.33 | 225.47 | 9.00 | 219.40 |

The data obtained shows that there is a substantial increase in the polarization shift for diseased ocular tissues (retina and RPE/choroid), compared to that of healthy tissues. The diseased eyes had been previously frozen, and were thawed before preparing the tissue samples for polarization measurements. The normal eyes had not been frozen. Based on previous observations of bovine retinal tissue at different times after freezing (see example 1, table III) one of ordinary skill in the art would infer that the polarization shift would have been even more pronounced in fresh diseased tissues.

Further, the polarization shift in human retinal tissue at 24 hours intervals was measured and is shown in table VII.

TABLE VII

Polarization shift (in degrees) of human retinal tissue over time

| Time (hrs) | Polarization Shift (degrees) |
|---|---|
| 0 | 13.0 |
| 24 | 11.5 |
| 48 | 5.0 |

It can be observed from table VII that the polarization change decreases significantly after 48 hours after sample preparation. During this period of time, the sample was kept refrigerated. The decrease in polarization shift can be attributed to the physiological degradation of the tissue, thereby changing the optical properties.

The observed variations in the polarization shifts between left and right eyes could be due to the minuscule differences in thickness of the tissue samples, particularly, when different locations were chosen to take the measurements. The RPE/choroidal tissue shows a higher degree of polarization shift than the retina tissue. The shift in the combined retinal and RPE/choroidal tissues are substantially higher. From the tables IV-VI, it can be determined that the higher the polarization shift, the lower the intensity of the scattered polarized light.

The invention may include a method and/or apparatus for assisting in the noninvasive diagnosis and treatment of diabetic retinopathy, macular degeneration, and other ocular diseases, including cancer detection.

The claims are not to be interpreted as including means-plus-function or step-plus-function limitations, unless such a limitation is explicitly recited in a given claim using the phrase(s) "means for" and/or "step for." The terms "a" or "an", as used herein, are defined as one or more than one. The terms "including" and/or "having", as used herein, are defined as comprising (i.e., open language). The term "coupled", as used herein, is defined as connected, although not necessarily directly, and not necessarily mechanically. The term "approximately", as used herein, is defined as at least close to a given value (e.g., preferably within 10% of, more preferably within 1% of, and most preferably within 0.1% of). The term "substantially", as used herein, is defined as at least approaching a given state (e.g., preferably within 10% of, more preferably within 1% of, and most preferably within 0.1% of).

Example 3

Introduction

An in-depth characterization of optical properties of human retinal and retinal pigment epithelium (RPE)/choroidal tissues has been performed. The indices of refraction of these ocular tissues were determined by applying Brewster's law. The inverse adding doubling method, based on the diffusion approximation and radiative transport theory is applied to the measured values of the total diffuse transmission, total diffuse reflection, and collimated transmission to calculate the optical absorption, and scattering of the human retinal and retinal pigment epithelium/choroidal tissues. The scattering anisotropy coefficients were calculated using an independent method which relates scattering angles and intensities. The resulting values have been analyzed using appropriate statistical methods.

Although there have been some studies on ocular melanin, a systematic investigation of the optical properties of intact ocular tissues is lacking. An in-depth characterization of optical properties of human retinal and choroidal tissues is presented. Melanin—a dark brown pigment abundantly present in human skin, retinal pigment epithelium (RPE) and choroid—is one of the primary biological components for light absorption and scattering. The chemical composition of melanin may be distinguished as sulfur-containing (pheomelanin) or sulfur-free (eumelanin), although most physiological melanins consist of two types of copolymer. Dryja et al. (1979) have shown that the melanin in RPE and choroid is similar with a low sulfur content of approximately 1%, indicating a largely eumelanin composition. The optical properties, however, do not differ significantly between eumelanin and pheomelanin. Melanin in the RPE/choroidal tissues strongly absorb the higher energy photons of ultraviolet radiation which are very phototoxic to the human eye. It is also believed that melanin-rich skin has natural resistance to skin cancer induced by solar exposure. A recent study has shown that the scattering is predominant over the absorption in melanin prepared from melanosomes isolated from bovine RPE. Biological materials (e.g. tissue and blood) are found to strongly scatter light. Mourant et al. (1998) have demonstrated that the light scattering property of biomaterials can be used as a diagnostic means for tissue pathology. Since medical laser applications for ocular diseases have steadily increased over the past several years and have become more complex, understanding the fundamental optical properties of ocular tissues is imperative because they influence the distribution and propagation of light in laser-irradiated tissues. Due to the complex nature of retinal and RPE/choroidal tissues, both of their absorption and scattering properties must be considered for medical applications of lasers.

The quantitative distribution of light intensity in biological media can be obtained from the solution of the radiative transport equation. The details of the radiative transport equation and the application of the Henyey-Greenstein scattering approximation to biological media can be found in Sardar et al. (2001). Although the transport equation is difficult to solve analytically for biological media due to the inherent inhomogeneities and irregularities in their physical shapes, only an approximate solution can be obtained by assuming homogeneity and regular geometry of the medium, and thereby an estimate of light intensity distribution can be obtained by solving the radiative transport equation. In order to solve the transport equation, the values for the absorption, scattering, and scattering anisotropy coefficients are needed. Thus, an appropriate experimental method is necessary to measure these fundamental optical properties. Although a single measurement of the total transmission through a sample of known thickness provides an attenuation coefficient for Beer's law of exponential decay, it is impossible to separate the attenuation due to absorption from the loss due to scattering. This problem, to some extent, has been resolved by the one-dimensional, two-flux Kubelka-Munk model which has been widely used to determine the absorption and scattering coefficients of biological media, provided the scattering is significantly dominant over the absorption. This model provides simple mathematical expressions for determining the optical parameters from the diffuse reflection and diffuse transmission measurements. In the past, researchers have applied the diffusion approximation to the transport equation to study biological media. Most notably, following the Kubelka-Munk model and diffusion approximation, an excellent experimental method has been described by Van Gemert et al. (1987) and Van Gemert and Star (1987) for determining the absorption and scattering coefficients and the scattering anisotropy factor.

More recently, an important numerical approach known as the Inverse Adding Doubling (IAD) method is employed to solve the transport equation. The IAD method has provided more accurate estimates of optical properties for turbid media than any other models previously used. Thus, in this example, the IAD method has been employed to determine both the absorption and scattering coefficients.

A short synopsis of the IAD model is provided here. Two dimensionless quantities used in the entire process of IAD are albedo (a) and optical depth ($\tau$) which are defined as follows:

$$a = \frac{\mu_s}{\mu_a + \mu_s} \quad (1)$$

and $$\tau = t(\mu_a + \mu_s) \quad (2)$$

where $\mu_a$ and $\mu_s$ are the absorption coefficient and scattering coefficient, respectively, t is the physical thickness of the sample and is measured in cm. The measured values of the total diffuse reflectance, total diffuse transmittance, and unscattered collimated transmittance are applied to the IAD algorithm in order to determine the optical absorption and scattering coefficients of the retinal and RPE/choroidal tissues. Further details of the IAD method can be found in Sardar et al. (2001).

Materials and Methods

Tissue Sample Preparation

One pair of healthy human eyes and one pair of diseased (neovascularized) human eyes were obtained from the National Disease Research Interchange (NDRI). The samples were procured under the stipulation that both sets of eyes were from donors with similar ages and were shipped "on ice" in order to preserve their natural optical properties. A total of three tissue samples were obtained from each set of eyes: retina, choroid and both retina and choroid (in stack, without compression).

The retinal and RPE/choroidal tissues from both the healthy and diseased human eyes were carefully dissected and individually placed between a pair of glass slides separated by two cover slips (spacers) at the two ends of glass slides. Special attention was paid in mounting the samples for optical measurements so that the irradiating light was directed into the samples from inside the eye cup. The purpose of placing the spacers was to prevent the glass slides from squeezing the tissues from its original, native shape to a compressed form. A small amount of vacuum grease was applied to the tissue between the glass slides in order to seal the open space between them so that the tissue was kept moist and retained in the space between the glass slides. These precautions were needed to maintain the integrity of tissue's physiological properties and also to make sure that its optical properties did not change due to the compression and/or dehydration of the sample.

Measurement of Index of Refraction

The indices of refraction of the retinal, choroidal, and RPE/choroidal tissues were determined by using the Brewster's law. According to the Brewster's law, the index of refraction (n) of the tissue can be determined by the following expression:

$$\tan(\theta_p) = n \quad (3)$$

where $\theta_p$ is the polarizing angle or Brewster's angle of incidence that is achieved only when the refracted and reflected beams at the sample surface were at right angles; then the reflected beam would be 100% polarized. The index of refraction of air is taken to be 1. Under these circumstances, for an incoming unpolarized wave made up of two incoherent orthogonal p-states (i.e., linearly polarized or plane-polarized), only the component polarized normal to the incident plane and therefore parallel to the surface will be reflected. Using the combination of a xenon arc lamp and a monochromator, a beam of unpolarized light at a known wavelength was directed onto the ocular tissue sample retained in between glass slides and mounted vertically on a calibrated table. The polarizing angle $\theta_p$ was found using a linear polarizing analyzer; the index of refraction was calculated for that particular wavelength using Eq. (3). This measurement was repeated for four different wavelengths selected through the monochromator.

Measurement of Scattering Anisotropy

Using an independent experimental technique, the scattering anisotropy coefficient (g) can also be obtained from the measurements of scattered light intensities (I) at various scattering angles (θ) using a goniometer table. The scattering anisotropy coefficient g is given by the average cosine of the scattering angle (θ) according to Eq. (4):

$$g = \frac{\sum_i (\cos\theta_i) I_i}{\sum_i I_i}, \tag{4}$$

where the sums are taken over all values (i) of the scattering angles and intensities. The scattering anisotropy coefficient (g) was obtained by irradiating the individual ocular tissue sample with a HeNe laser. The sample was placed in the sample holder affixed to the center of the goniometer table. The measurements were taken using an Oriel (model 77341) photomultiplier tube (PMT) mounted at the edge of the goniometer table. The PMT was powered by a Bertan (model 215) power supply. The HeNe laser beam was aligned at a right angle with respect to the plane of the tissue sample, and the PMT was attached to an adjustable pointer which could be rotated around the circular goniometer table for measuring the scattered intensities at different angles. The scattered light intensity was measured between 0° and 180° at an increment of 1° from 0° to 10° of scattering angle, and an increment of 5° above 10° of scattering angle. Further experimental details can be found in Sardar et al. (2001).

Measurement of Diffuse Reflectance and Transmittance

The total diffuse reflectance and total diffuse transmittance were measured using two identical integrating spheres (Oriel model 70451). The tissue sample was placed in a specially designed holder which coupled the two integrating spheres. The measurements were performed on the retinal, choroidal, and RPE/choroidal tissues at 514, 501, 488, and 476 mm from an Argon ion laser (Spectra Physics model 2025). Although the maximum output power of the Argon ion laser varied from 1 to 2 W, the average output power was kept at its minimum value of about 5 mW for all optical measurements. The laser beam diameter at $1/e^2$ was 1.25 mm and beam divergence was 0.70 mrad at 488 nm.

Figure 3:
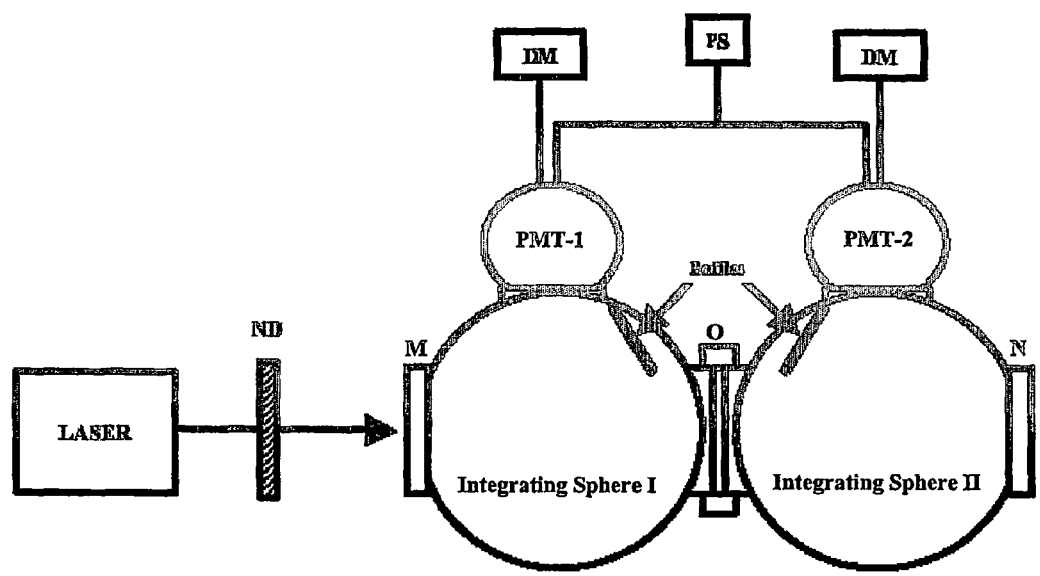
FIG. 3 is a diagram of an experimental schematic for the diffuse reflection and transmission measurements on the retinal, choroidal, and RPE/choroidal tissues. In this figure, DM stands for Digital Multimeter, PS for Power Supply, PMT for Photomultiplier Tube, and ND for Neutral Density Filter.

The schematic of the experimental setup for measuring the total diffuse reflectance and total diffuse transmittance is shown in FIG. 3. The experimental setup was similar to that used by Beek et al. (1997). The laser beam was directed into the entrance port M of integrating sphere 1, whose exit port is coupled with the entrance port of integrating sphere 2; the sample was mounted at the coupling port O. The exit port N of integrating sphere 2 was covered with a cap with a reflective surface identical to that of the integrating spheres. The diameter of each sphere was 6 inches and each port had a diameter of 1 inch. Light leaving the sample reflected multiple times from the inner surfaces of the spheres before reaching the PMTs. Reflecting baffles within the spheres shielded the PMTs from the direct light from the sample. Port M was equipped with a variable aperture so that the beam diameter could be appropriately controlled. The reflected and transmitted light intensities were detected by two identical PMTs (Oriel model 77341); these were attached to the two measuring ports of the integrating spheres 1 and 2. The PMTs were powered by a common power supply (Bertan model 215). The signals from the PMTs were measured by two identical Fluke digital multimeters (model 77 series II). The measured light intensities were then utilized to determine the total diffuse reflectance $R_d$ and total diffuse transmittance $T_d$ by the following expressions:

$$R_d = \frac{X_r - Y}{Z_r - Y} \tag{5}$$

and $$T_d = \frac{X_t - Y}{Z_t - Y} \tag{6}$$

where $X_r$ is the reflected intensity detected by the PMT-1 with the sample at O, $Z_r$ is the incident intensity detected by the PMT-1 without the sample at O and with the reflective surface at the exit port of integrating sphere 1, $X_t$ is the transmitted intensity detected by the PMT-2 with the sample at O and $Z_t$ is the incident intensity detected by the PMT-2 with no sample at O and with a reflective surface at N, and Y is the correction factor for the stray light measured by the PMTs 1 and 2 with no sample at O nor the reflective surface at N.

Measurement of Collimated Transmittance

The unscattered collimated transmittance $T_c$ was measured to determine the total attenuation coefficient. The collimated laser beam intensities were measured by placing an integrating sphere approximately 2 m behind the sample so that the photons scattered off the sample would not be able to enter the aperture of approximately 3 mm in diameter at the entrance port of the sphere. The sample was aligned at a right angle with respect to the incident beam. The collimated transmittance $T_c$ was calculated by the following relation:

$$T_c = \frac{X_c}{Z_c} \tag{7}$$

where $X_c$ is the collimated light intensity detected by a PMT (Oriel model 77341) attached to the measuring port of the integrating sphere and $Z_c$ is the incident light intensity detected by the PMT with no sample in the light path; the reflective surface was placed at the exit port of the integrating sphere in both cases. Additional details on the experimental design can be found in Sardar et al. (2001).

Inverse Adding Doubling (IAD) Method

In order to solve the radiative transport equation, the IAD algorithm must be supplied with the experimentally determined values of the total diffuse reflectance ($R_d$), total diffuse transmittance ($T_d$), and collimated transmittance ($T_c$). The IAD algorithm iteratively chooses the values for the dimensionless quantities: a and τ, defined in Eqs. (1) and (2), respectively, and then adjusts the value of the scattering anisotropy coefficient (g) until it matches the measured values of $R_d$ and $T_d$. The values of a and τ provided by the IAD method are then used to calculate the absorption coefficient ($\mu_a$) and scattering coefficient ($\mu_s$) using Eqs. (1) and (2).

Results and Discussion

The indices of refraction (n) of retina and RPE/choroid were measured by the Brewster's method at 450, 500, 550, and 600 nm from a xenon lamp. The measured n values varied from 1.34 to 1.38. The refractive indices of intact bovine retina are about 10% higher than those for melanin isolated from the bovine RPE melanosomes. Measurements were repeated three times at each of these wavelengths, and the values agreed to within 5%. The scattering anisotropy coefficients of retinal and RPE/choroidal tissues were determined from the goniometric measurements to be: 0.79 for retina, 0.78 for RPE/choroid and 0.76 for retina and RPE/choroid (in stack). For all of the IAD calculations, we have used the average values of: 1.36 for retina, 1.38 for RPE/choroid and 1.39 for both retina and RPE/choroid (in stack). These values were used to calculate each respective IAD value.

from the values of a and $\tau$. The absorption coefficient ($\mu_a$), scattering coefficient ($\mu_s$), total attenuation coefficient ($\mu_t=\mu_a+\mu_s$), penetration depth ($1/\mu_t$), albedo (a), and optical depth ($\tau$) for the retina, RPE/choroid and retina/choroid (in stack) are given in Tables VIII-X, respectively.

In both the healthy and diseased retinal tissues, the scattering was found to be significantly higher than the absorption; while in the RPE/choroidal tissues, both the absorption and scattering were found to be comparable. However, the absorption coefficients of the RPE/choroid are consistently higher than those of retina. This is believed to be due to the fact that the RPE/choroid is physiologically more opaque and contains melanin. The values of the attenuation coefficients of retina can be attributed to some inadvertent cross-contamination of the retina with melanin granules from the RPE during

TABLE VIII

The wavelength ($\lambda$) dependent optical properties of human retina as determined by the IAD method using the measured diffuse reflectance ($R_d$), diffuse transmittance ($T_d$), and collimated transmittance ($T_c$). The margin of errors are given below the measured values.

| | | | | | | | IAD | | | |
| --- | --- | --- | --- | --- | --- | --- | --- | --- | --- | --- |
| | Wavelength $\lambda$ | Experimental | | | | | $\mu_a$ | $\mu_s$ | $\mu_t$ | $1/\mu_t$ |
| Condition | (nm) | $R_d$ | $T_d$ | $T_c$ | a | $\tau$ | (cm$^{-1}$) | (cm$^{-1}$) | (cm$^{-1}$) | (cm) |
| healthy | 476 | 0.140 ± 0.003 | 0.74 ± 0.01 | 0.004 ± 0.006 | 0.991 | 5.36 | 1.79 | 196.73 | 198.52 | 0.0050 |
| | 488 | 0.130 ± 0.006 | 0.72 ± 0.02 | 0.002 ± 0.004 | 0.988 | 5.99 | 2.66 | 219.19 | 221.85 | 0.0045 |
| | 501 | 0.099 ± 0.002 | 0.71 ± 0.05 | 0.003 ± 0.001 | 0.982 | 5.87 | 3.91 | 213.49 | 217.40 | 0.0046 |
| | 514 | 0.091 ± 0.002 | 0.74 ± 0.04 | 0.003 ± 0.007 | 0.983 | 5.67 | 3.57 | 206.43 | 210.00 | 0.0048 |
| diseased | 476 | 0.330 ± 0.005 | 0.35 ± 0.06 | 0.003 ± 0.008 | 0.979 | 5.91 | 4.60 | 214.29 | 218.89 | 0.0046 |
| | 488 | 0.176 ± 0.004 | 0.33 ± 0.06 | 0.005 ± 0.008 | 0.949 | 5.27 | 9.95 | 185.23 | 195.18 | 0.0051 |
| | 501 | 0.513 ± 0.004 | 0.35 ± 0.05 | 0.004 ± 0.008 | 0.992 | 5.50 | 1.63 | 202.07 | 203.70 | 0.0049 |
| | 514 | 0.142 ± 0.004 | 0.41 ± 0.05 | 0.002 ± 0.010 | 0.961 | 6.27 | 9.06 | 223.17 | 232.23 | 0.0043 |

The total diffuse reflectance ($R_d$), total diffuse transmittance ($T_d$), and the collimated transmittance ($T_c$) were measured on the retinal and RPE/choroidal tissues at 476, 488, 501 and 514 nm. These values are given in Tables VIII-X. The margin of errors of the measurements of $R_d$, $T_d$ and $T_c$ are also given in Tables VIII-X. These values, along with the measured values of the index of refraction and the scattering anisotropy coefficient, were input into the IAD program. The output of the IAD program provided the dimensional quantities a and $\tau$, defined by Eqs. (1) and (2), respectively. The absorption and scattering coefficients were then calculated sample preparation. Since the attenuation coefficients of RPE/choroid at all wavelengths investigated are lower than those of retina, the penetration depths in RPE/choroid are larger than those in retina. It is important to note that when comparing the retina/choroid samples (in stack), the diseased set of eyes have higher absorption coefficient values—possibly due to an increased number of localized neovascularizations in the ocular tissue. Also, the scattering coefficients for the diseased eyes were lower than those of the healthy eyes; one explanation for this is that the neovascularizations have a slight effect on the geometry of the light-tissues interaction.

TABLE IX

The wavelength ($\lambda$) dependent optical properties of human choroid as determined by the IAD method using the measured diffuse reflectance ($R_d$), diffuse transmittance ($T_d$), and collimated transmittance ($T_c$). The margin of errors are given below the measured values.

| | | | | | | | IAD | | | |
| --- | --- | --- | --- | --- | --- | --- | --- | --- | --- | --- |
| | Wavelength $\lambda$ | Experimental | | | | | $\mu_a$ | $\mu_s$ | $\mu_t$ | $1/\mu_t$ |
| Condition | (nm) | $R_d$ | $T_d$ | $T_c$ | a | $\tau$ | (cm$^{-1}$) | (cm$^{-1}$) | (cm$^{-1}$) | (cm) |
| healthy | 476 | 0.060 ± 0.002 | 0.01 ± 0.03 | 0.002 ± 0.001 | 0.476 | 6.07 | 70.68 | 64.21 | 134.89 | 0.0074 |
| | 488 | 0.054 ± 0.004 | 0.01 ± 0.02 | 0.001 ± 0.003 | 0.567 | 6.67 | 64.18 | 84.04 | 148.22 | 0.0067 |
| | 501 | 0.054 ± 0.002 | 0.01 ± 0.02 | 0.003 ± 0.003 | 0.540 | 5.86 | 59.90 | 70.32 | 130.22 | 0.0077 |
| | 514 | 0.047 ± 0.002 | 0.01 ± 0.01 | 0.002 ± 0.005 | 0.596 | 6.39 | 57.37 | 84.63 | 142.00 | 0.0070 |
| diseased | 476 | 0.325 ± 0.005 | 0.04 ± 0.04 | 0.001 ± 0.004 | 0.935 | 7.21 | 10.41 | 149.81 | 160.22 | 0.0062 |
| | 488 | 0.184 ± 0.002 | 0.04 ± 0.01 | 0.001 ± 0.006 | 0.887 | 7.21 | 18.11 | 142.12 | 160.23 | 0.0062 |
| | 501 | 0.109 ± 0.004 | 0.03 ± 0.03 | 0.001 ± 0.005 | 0.807 | 6.76 | 28.99 | 121.23 | 150.22 | 0.0067 |
| | 514 | 0.118 ± 0.003 | 0.05 ± 0.05 | 0.001 ± 0.006 | 0.854 | 6.86 | 22.26 | 130.19 | 152.45 | 0.0066 |

The data has been analyzed using a one-way analysis of variance (ANOVA) test to confirm that there was a significant statistical difference between each respective tissue sample when comparing the two tissue conditions—healthy and diseased. Each ANOVA test confirmed that there were significant differences (at $\alpha=0.05$) between each tissue/condition. One of the assumptions used in this analysis was that the respective attenuation coefficients were independent of wavelength. This assumption of homogeneity within each experimental condition can be tested used a $X^2$ test, however, the expected values for these tests are not well established. Thus, because there was no observable wavelength-dependence in the reflectance and transmittance values, the assumption of wavelength-independence seems valid. Again, the fact that there was a significant difference between the optical properties of the healthy and diseased eyes signals that the characterization of these ocular tissues can yield important information regarding early detection/treatment of diabetic retinopathy.

TABLE X

The wavelength ($\lambda$) dependent optical properties of human retina and choroid (in stack) as determined by the IAD method using the measured diffuse reflectance ($R_d$), diffuse transmittance ($T_d$), and collimated transmittance ($T_c$). The margin of errors are given below the measured values.

| | | Experimental | | | | | IAD | | | |
|---|---|---|---|---|---|---|---|---|---|---|
| Condition | Wavelength $\lambda$ (nm) | $R_d$ | $T_d$ | $T_c$ | a | $\tau$ | $\mu_a$ (cm$^{-1}$) | $\mu_s$ (cm$^{-1}$) | $\mu_t$ (cm$^{-1}$) | $1/\mu_t$ (cm) |
| healthy | 476 | 0.125 ± 0.003 | 0.01 ± 0.01 | 0.001 ± 0.004 | 0.724 | 6.76 | 35.88 | 94.12 | 130.00 | 0.0077 |
| | 488 | 0.090 ± 0.004 | 0.01 ± 0.02 | 0.001 ± 0.005 | 0.665 | 6.67 | 42.97 | 85.30 | 128.27 | 0.0078 |
| | 501 | 0.082 ± 0.002 | 0.01 ± 0.05 | 0.003 ± 0.001 | 0.515 | 5.86 | 54.66 | 58.04 | 112.70 | 0.0089 |
| | 514 | 0.083 ± 0.003 | 0.01 ± 0.04 | 0.003 ± 0.003 | 0.565 | 5.69 | 47.60 | 61.82 | 109.42 | 0.0091 |
| diseased | 476 | 0.298 ± 0.001 | 0.07 ± 0.07 | 0.001 ± 0.007 | 0.944 | 7.55 | 8.13 | 137.06 | 145.19 | 0.0069 |
| | 488 | 0.175 ± 0.004 | 0.06 ± 0.03 | 0.001 ± 0.002 | 0.906 | 7.55 | 13.65 | 131.54 | 145.19 | 0.0069 |
| | 501 | 0.070 ± 0.003 | 0.04 ± 0.01 | 0.001 ± 0.004 | 0.800 | 7.21 | 27.73 | 110.92 | 138.65 | 0.0072 |
| | 514 | 0.107 ± 0.004 | 0.05 ± 0.02 | 0.001 ± 0.006 | 0.848 | 7.21 | 21.08 | 117.58 | 138.65 | 0.0072 |

On a broader scale, the actual values of the absorption and scattering coefficients for the retinal and RPE/choroidal tissues reported in this example have importance for practical application requiring the prediction of light transport through pigmented tissue (e.g. in the design of treatment models for laser-induced thermotherapy or photodynamic therapy in the eye, where the degree of pigmentation at the target sites may vary). Variable pigmentation obviously complicates the laser dosimetry for such treatment modes, because the amount of light delivered will have to be adjusted based on the amount of tissue pigmentation in order to achieve some standard clinical effect.

Example 4

Introduction

An in-depth characterization of optical properties of bovine retinal and retinal pigment epithelium (RPE)/choroidal tissues has been performed. The indices of refraction of these ocular tissues were determined by applying Brewster's law. The inverse adding doubling method based on the diffusion approximation and radiative transport theory is applied to the measured values of the total diffuse transmission, total diffuse reflection, and collimated transmission to calculate the optical absorption, scattering, and scattering anisotropy coefficients of the bovine retinal and retinal pigment epithelium/choroidal tissues. The values of the optical properties obtained from the inverse adding doubling method are compared with those generated by the Monte Carlo simulation technique. The optical polarization measurements are also performed on bovine retinal tissues. Our studies show that both retina and retinal pigment epithelium/choroid possess strong polarization characteristics.

Although there have been some studies on ocular melanin, a systematic investigation of the optical properties of intact ocular tissues is lacking. An in-depth characterization of optical properties of bovine retinal and retinal pigment epithelium (RPE)/choroidal tissues is presented. Melanin, a dark brown pigment abundantly present in human skin, retina and RPE/choroidal, is one of the primary biological components for light absorption and scattering. The chemical composition of melanin may be distinguished as sulfur-containing (pheomelanin) or sulfur-free (eumelanin), although most physiological melanins consist of two types of copolymer. Dryja et al. (1979) have shown that the melanin in retina and RPE/choroid is similar with a low sulfur content of approximately 1%, indicating a largely eumelanin composition. The optical properties, however, do not differ significantly between eumelanin and pheomelanin. Melanin in the retinal and RPE/choroidal tissues strongly absorbs the higher energy photons of ultraviolet radiation which are very phototoxic to the human eye. It is also believed that melanin-rich skin has natural resistance to skin cancer induced by solar exposure. A recent study by Sardar et al. (2001) has shown that the scattering is predominant over the absorption in melanin prepared from melanosomes isolated from bovine RPE. Biological materials (e.g. tissue and blood) are found to strongly scatter light. Mourant et al. (1998) have demonstrated that this light scattering property of biomaterials can be used as a diagnostic means for tissue pathology. Since medical laser applications for ocular diseases have steadily increased over the past several years and have become more complex, understanding the fundamental optical properties of ocular tissues is imperative because they influence the distribution and propagation of light in laser-irradiated tissues. Due to the complex nature of retinal and RPE/choroidal tissues, both of their absorption and scattering properties must be considered for medical applications of lasers.

The quantitative distribution of light intensity in biological media can be obtained from the solution of the radiative transport equation. The details of the radiative transport equation and the application of the Henyey-Greenstein scattering approximation to biological media can be found in Sardar et al. (2001). Although the transport equation is difficult to solve analytically for biological media due to the inherent inhomogeneities and irregularities in their physical shapes, only an approximate solution can be obtained by assuming homogeneity and regular geometry of the medium, and thereby an estimate of light intensity distribution can be obtained by solving the radiative transport equation. In order to solve the transport equation, the values for the absorption, scattering, and scattering anisotropy coefficients are needed. Therefore, an appropriate experimental method is necessary to measure these fundamental optical properties. Although a single measurement of the total transmission through a sample of known thickness provides an attenuation coefficient for the Beer's law of exponential decay, it is impossible to separate the attenuation due to absorption from the loss due to scattering. This problem, to some extent, has been resolved by the one-dimensional, two-flux Kubelka-Munk model which has been widely used to determine the absorption and scattering coefficients of biological media, provided the scattering is significantly dominant over the absorption. This model provides simple mathematical expressions for determining the optical parameters from the diffuse reflection and diffuse transmission measurements. In the past, researchers have applied the diffusion approximation to the transport equation to study biological media. Most notably, following the Kubelka-Munk model and diffusion approximation, an excellent experimental method has been described by Van Gemert et al. (1987) and Van Gemert and Star (1987) for determining the absorption and scattering coefficients and the scattering anisotropy factor.

Even though the general solution is not available, an elaborate numerical solution is possible using the Monte Carlo (MC) simulation technique. More recently, an important numerical approach known as the Inverse Adding Doubling (IAD) method is employed to solve the transport equation. Both the IAD method and MC simulation technique have provided more accurate estimates of optical properties for turbid media than any other models previously used. Therefore, the IAD method has been employed to determine both the absorption and scattering coefficients. A short synopsis of the IAD model is provided here. Two dimensionless quantities used in the entire process of IAD are albedo a and optical depth $\tau$ which are defined as follows:

$$a = \mu_s / (\mu_s + \mu_a) \quad (8)$$

and $$\tau = t(\mu_s + \mu_a), \quad (9)$$

where $\mu_a$ and $\mu_s$ are the absorption coefficient and scattering coefficient, respectively, t is the physical thickness of the sample and is measured in cm. The measured values of the total diffuse reflectance, total diffuse transmittance, and unscattered collimated transmittance are applied to the IAD algorithm in order to determine the optical absorption and scattering coefficients of the retinal and RPE/choroidal tissues. Further details of the IAD method can be found in Sardar et al. (2001).

The retinal and retinal pigment epithelium (RPE)/choroidal tissues are found to be inherently birefringent and thereby possess the important optical polarization property. Based on their geometry and optical properties, these tissues have intrinsic property of altering the polarization of incident light in every scattering event. Therefore, in addition to characterizing the fundamental optical properties, the polarization measurements have also been performed on bovine retinal and RPE/choroidal tissues.

Materials and Methods

Retinal and RPE/Choroidal Tissue Preparation

Samples of the retinal and RPE/choroidal tissues were prepared from fresh bovine eyes (left and right) that were obtained from the local slaughter plants; the eyes were preserved on ice and transported to our laboratory in less than an hour. Upon arrival in the lab, anterior segments including cornea, lens, and aqueous vitreous humor fluid were removed from the eyes. The retina was then carefully lifted from the posterior eye cup and mounted between two glass slides. The RPE/choroid was subsequently removed from the eye and similarly mounted. The thicknesses of the retinal and RPE/choroidal tissues were approximately 0.15 and 0.10 mm, respectively. A small amount of vacuum grease was applied to the edges of the glass slides in order to maintain the moisture of the tissue sample. All of the data was collected at room temperature within two hours from the slaughter of the animals.

Measurement of Index of Refraction

The indices of refraction of the retinal and RPE/choroidal tissues were determined by using the Brewster's law. According to the Brewster's law, the index of refraction (n) of the tissue can be determined by the following expression:

$$\tan \theta_p = n, \quad (10)$$

where $\theta_p$ is the polarizing angle or Brewster's angle of incidence that is achieved only when the refracted and reflected beams at the sample surface were at right angles; then the reflected beam would be 100% polarized. The index of refraction of air is taken to be 1. Under these circumstances, for an incoming unpolarized wave made up of two incoherent orthogonal p-states (i.e., linearly polarized or plane-polarized), only the component polarized normal to the incident plane and therefore parallel to the surface will be reflected. Using the combination of a xenon arc lamp and a monochromator, a beam of unpolarized light at a known wavelength was directed onto the ocular tissue sample retained in between glass slides and mounted vertically on a calibrated table. The polarizing angle $\theta_p$ was found using a linear polarizing analyzer; the index of refraction was calculated for that particular wavelength using the Eq. (10). This measurement was repeated for four different wavelengths selected through the monochromator.

Measurement of Scattering Anisotropy

Using an independent experimental technique, the scattering anisotropy coefficient g can also be obtained from the measurements of scattered light intensities (I) at various scattering angles ($\theta$) using a goniometer table. The scattering anisotropy coefficient g is given by the average cosine of the scattering angle $\theta$ according to Eq. (11):

$$g = \frac{\sum_i (\cos \theta_i) I_i}{\sum_i I_i}, \quad (11)$$

where the sums are taken over all values (i) of the scattering angles and intensities. The scattering anisotropy coefficient (g) was obtained by irradiating the individual ocular tissue sample with a HeNe laser. The sample was placed in the sample holder affixed to the center of the goniometer table. The measurements were taken using an Oriel (model 77341) photomultiplier tube (PMT) mounted at the edge of the goniometer table. The PMT was powered by a Bertan (model 215) power supply. The HeNe laser beam was aligned at a right angle with respect to the plane of the tissue sample, and the PMT was attached to an adjustable pointer which could be rotated around the circular goniometer table for measuring the scattered intensities at different angles. The scattered light intensity was measured between 0° and 180° at an increment of 1° from 0° to 10° of scattering angle, and an increment of 5° above 10° of scattering angle. Further experimental details can be found in Sardar et al. (2001).

Measurement of Diffuse Reflectance and Transmittance

The total diffuse reflectance and total diffuse transmittance were measured using the two identical integrating spheres (Oriel model 70451). The tissue sample was placed in a specially designed holder which coupled the two integrating spheres. The measurements were performed on the retinal and RPE/choroidal tissues at 514, 501, 488, and 476 nm from an Argon ion laser (Spectra Physics model 2025). Although the maximum output power of the Argon ion laser varied from 1 to 2 W, the average output power was kept at its minimum value of about 5 mW for all optical measurements. The laser beam diameter at $1/e^2$ was 1.25 mm and beam divergence was 0.70 mrad at 488 nm.

The schematic of the experimental setup for measuring the total diffuse reflectance and total diffuse transmittance is shown in FIG. 3. The experimental setup was similar to that used by Beek et al. (1997). The laser beam was directed into the entrance port M of integrating sphere 1, whose exit port is coupled with the entrance port of integrating sphere 2; the sample was mounted at the coupling port O. The exit port N of integrating sphere 2 was covered with a cap with a reflective surface identical to that of the integrating spheres. The diameter of each sphere was 6 inches and each port had a diameter of 1 inch. Light leaving the sample reflected multiple times from the inner surfaces of the spheres before reaching the PMTs. Reflecting baffles within the spheres shielded the PMTs from the direct light from the sample. Port M was equipped with a variable aperture so that the beam diameter could be appropriately controlled. The reflected and transmitted light intensities were detected by two identical PMTs (Oriel model 77341); these were attached to the two measuring ports of the integrating spheres 1 and 2. The PMTs were powered by a common power supply (Bertan model 215). The signals from the PMTs were measured by two identical Fluke digital multimeters (model 77 series II). The measured light intensities were then utilized to determine the total diffuse reflectance $R_d$ and total diffuse transmittance $T_d$ by the following expressions:

$$R_d = \frac{X_r - Y}{Z_r - Y} \quad (12)$$

and $$T_d = \frac{X_t - Y}{Z_t - Y} \quad (13)$$

where $X_r$ is the reflected intensity detected by the PMT-1 with the sample at O, $Z_r$ is the incident intensity detected by the PMT-1 without the sample at O and with the reflective surface at the exit port of integrating sphere 1, $X_t$ is the transmitted intensity detected by the PMT-2 with the sample at O and $Z_t$ is the incident intensity detected by the PMT-2 with no sample at O and with a reflective surface at N, and Y is the correction factor for the stray light measured by the PMTs 1 and 2 with no sample at O nor the reflective surface at N.

Measurement of Collimated Transmittance

The unscattered collimated transmittance $T_c$ was measured to determine the total attenuation coefficient. The collimated laser beam intensities were measured by placing an integrating sphere approximately 2 m behind the sample so that the photons scattered off the sample would not be able to enter the aperture of approximately 3 mm in diameter at the entrance port of the sphere. The sample was aligned at a right angle with respect to the incident beam. The collimated transmittance $T_c$ was calculated by the following relation:

$$T_c = \frac{X_c}{Z_c} \quad (14)$$

where $X_c$ is the collimated light intensity detected by a PMT (Oriel model 77341) attached to the measuring port of the integrating sphere and $Z_c$ is the incident light intensity detected by the PMT with no sample in the light path; the reflective surface was placed at the exit port of the integrating sphere in both cases. Additional details on the experimental design can be found in Sardar et al. (2001).

Inverse Adding Doubling (IAD) Method

In order to solve the radiative transport equation, the IAD algorithm must be supplied with the experimentally determined values of the total diffuse reflectance ($R_d$), total diffuse transmittance ($T_d$), and collimated transmittance ($T_c$). The IAD algorithm iteratively chooses the values for the dimensionless quantities: a and $\tau$, defined in Eqs. (8) and (9), respectively, and then adjusts the value of the scattering anisotropy coefficient g until it matches the measured values of $R_d$ and $T_d$. The values of a and $\tau$ provided by the IAD method are then used to calculate the absorption coefficient ($\mu_a$) and scattering coefficient ($\mu_s$) using Eqs. (8) and (9).

Monte Carlo (MC) Simulation

The accuracy of values of the absorption coefficient ($\mu_a$) and scattering coefficient ($\mu_s$) determined by the IAD method was verified by the MC simulation technique. The MC simulation uses the stochastic model to simulate the light interaction in biological media. The $\mu_a$ and $\mu_s$ calculated by the IAD method, along with the experimentally determined index of refraction n and scattering anistropy coefficient g were used to compute the $R_d$ and $T_d$. These values were then compared for accuracy with the experimental values of $R_d$ and $T_d$. A detailed theoretical description of the MC model in biological media is given by Prahl et al. (1989).

Measurement of Polarization Shift

Figure 4:
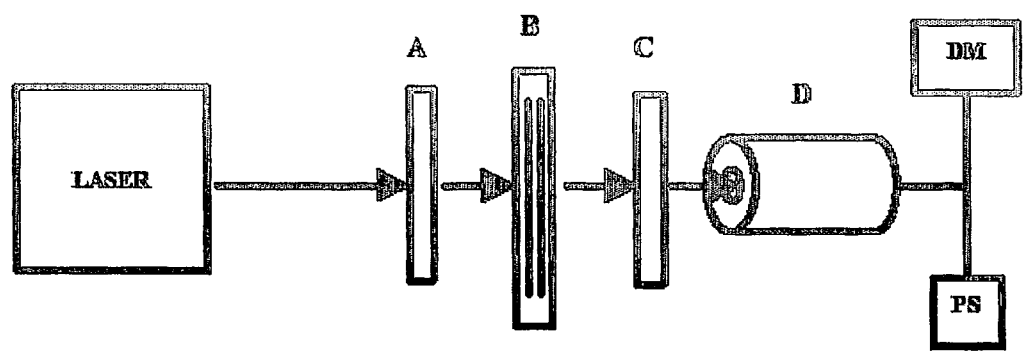
FIG. 4 is a diagram of an experimental setup for measuring the polarization shifts in degrees on the retinal tissue. In this figure, A stands for Linear Polarizer, B for Sample Holder, C for Linear Polarizer/Analyzer, D for Detector, PS for Power Supply, and DM for Digital Multimeter.

The experimental setup for polarization measurements for the retinal tissue is shown in FIG. 4. The He—Ne laser (Uniphase model 1101P) with a power of 4 mW and beam diameter of 3 mm was passed through a linear polarizer placed in front of the retinal sample position beyond which was placed a second linear polarizer (analyzer). The polarizers were obtained from Oriel Corporation (Oriel model 25010). Behind the analyzer was placed a photodiode detector that was provided a low bias voltage from a power supply (Cenco model 31382); the photodiode was connected to a multimeter (Fluke model 77 series II). First, the polarizer (without the sample and analyzer in the laser path) was rotated until the maximum laser light intensity was obtained, indicating that the laser beam is completely polarized. Once the maximum laser intensity was achieved, the analyzer was placed behind a pair of blank slides (without the sample in the light path). The analyzer was then rotated to maximize the light intensity so that the transmission axes of the polarizer and analyzer are parallel. Thus, the reference condition was established with a pair of blank slides placed in the sample position. The blank slides were then replaced by the retinal sample placed between the polarizer and analyzer. The polarization shift of the scattered laser light was observed and the shift was determined by rotating the analyzer until maximum light intensity was achieved. Measurements were taken at three different locations on each sample; an average of the three measurements was taken for each location.

Figure 5:
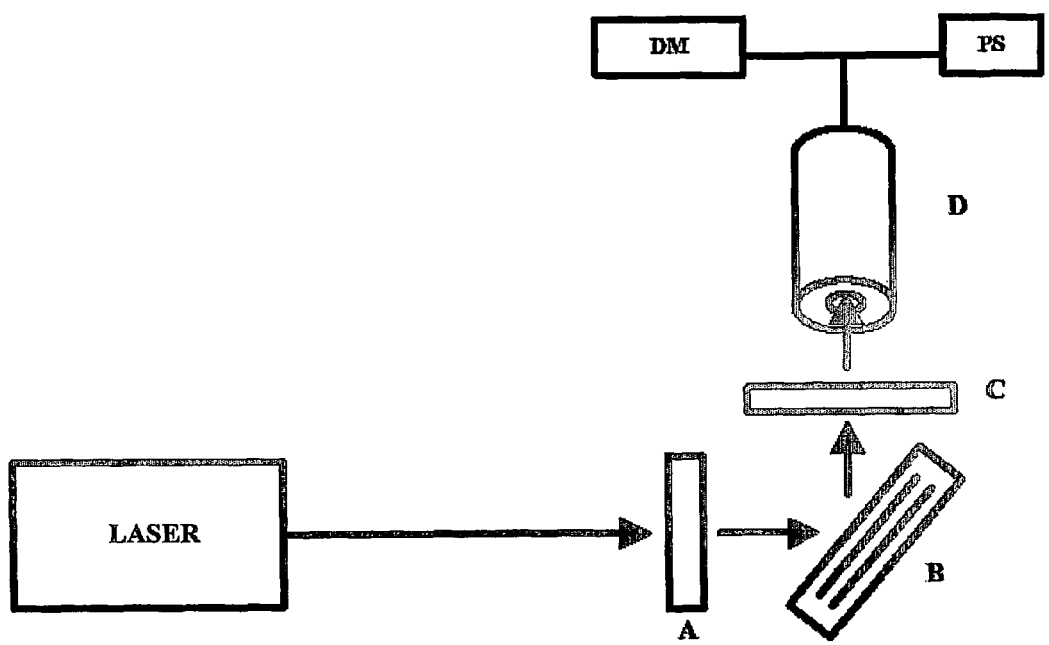
FIG. 5 is a diagram of an experimental setup for measuring the polarization shifts in degrees of all RPE/choroidal tissue and the combination of retinal and RPE/choroidal tissues in stack. In this figure, A stands for Linear Polarizer, B for Sample Holder, C for Linear Polarizer/Analyzer, D for Detector, PS for Power Supply, and DM for Digital Multimeter.

Owing to its opacity in nature, the beam cannot penetrate the RPE/choroidal tissue sample. Therefore, a simple modification of the experimental setup is made for measurements of the polarized light scattered off the RPE/choroidal tissue, and is shown in FIG. 5. A clean glass slide was placed in the sample holder and the scattered beam was directed at approximately a right angle with respect to the direction of the incident laser beam. The analyzer and photodiode were aligned with the direction of the most intense scattered beam. The same technique as described above was employed to assure that the transmission axes of both polarizer and analyzer are parallel. The glass slide was then replaced by the RPE/choroidal tissue sample. The polarization shift for the RPE/choroid was determined in the same manner as done for retina. For the RPE/choroidal sample, measurements were taken at three different locations on the sample; an average of the three measurements was taken at each location. This was done to minimize the uncertainties in the measurements. The same experimental methodology was utilized for the polarization measurements on the retinal and RPE/choroidal tissues placed together. In this case, retinal tissue sample was placed in front of the RPE/choroidal tissue sample.

Results and Discussion

The indices of refraction (n) of retina and RPE/choroid were measured by the Brewster's method at 450, 500, 550, and 600 nm from a xenon lamp. The measured n values varied from 1.34 to 1.38. The refractive indices of intact bovine retina are about 10% higher than those for melanin isolated from the bovine RPE melanosomes. Measurements were repeated three times at each of these wavelengths, and the values agreed to within 5%. The scattering anisotropy coefficients of retinal and RPE/choroidal tissues were determined to be between 0.92 and 0.96 from the goniometric measurements. For all of the IAD calculations, we have used the average values of 1.36 and 0.94 for the index of refraction n and the scattering anisotropy coefficient g, respectively.

TABLE XI

The wavelength ($\lambda$) dependent absorption coefficient ($\mu_a$), scattering coefficient ($\mu_s$), total attenuation coefficient ($\mu_t$), mean free path ($1/\mu_t$), albedo (a), and optical depth ($\tau$) as determined by IAD using the measured diffuse reflectance ($R_d$), diffuse transmittance ($T_d$), and collimated transmittance ($T_c$) for retina. The margin of errors are given below the measured values.

| Wavelength $\lambda$ (nm) | Experimental | | | | | IAD | | | |
|---|---|---|---|---|---|---|---|---|---|
| | $R_d$ | $T_d$ | $T_c$ | a | $\tau$ | $\mu_a$ (cm$^{-1}$) | $\mu_s$ (cm$^{-1}$) | $\mu_t$ (cm$^{-1}$) | $1/\mu_t$ (cm) |
| 514 | 0.061 ± 0.005 | 0.79 ± 0.06 | 0.110 ± 0.008 | 0.952 | 2.16 | 10.4 | 205 | 215.4 | 0.00465 |
| 501 | 0.060 ± 0.004 | 0.76 ± 0.76 | 0.112 ± 0.008 | 0.939 | 2.15 | 13.0 | 202 | 215.0 | 0.00465 |
| 488 | 0.058 ± 0.004 | 0.70 ± 0.05 | 0.112 ± 0.008 | 0.915 | 2.14 | 18.2 | 196 | 214.2 | 0.00467 |
| 476 | 0.054 ± 0.004 | 0.65 ± 0.05 | 0.131 ± 0.010 | 0.882 | 1.99 | 23.5 | 175 | 198.5 | 0.00504 |

The total diffuse reflectance ($R_d$), total diffuse transmittance ($T_d$), and the collimated transmittance ($T_c$) were measured on the retinal and RPE/choroidal tissues at 514, 501, 488 and 476 nm. These values are given in Tables XI and XII. These measurements were repeated three time; the coefficient of variation of the measurements was approximately 4%. These values, along with the measured values of the index of refraction and the scattering anisotropy coefficient, were input into the IAD program. The output of the IAD program provided the dimensional quantities a and $\tau$, defined by Eqs. (8) and (9), respectively. The absorption and scattering coefficients were then calculated from the values of a and $\tau$. The absorption coefficient ($\mu_a$), scattering coefficient ($\mu_s$), total attenuation coefficient ($\mu_t = \mu_a + \mu_s$), penetration depth ($1/\mu_t$), albedo (a), and optical depth ($\tau$) for the retinal and RPE/choroidal tissues are given in Tables XI and XII, respectively. The measured values of $R_d$ and $T_d$ used to calculate $\mu_a$ and $\mu_s$ by the IAD method were compared with those generated by the MC simulation technique. These values are given in Tables XIII and XIV.

TABLE XII

The wavelength ($\lambda$) dependent absorption coefficient ($\mu_a$), scattering coefficient ($\mu_s$), total attenuation coefficient ($\mu_t$), mean free path ($1/\mu_t$), albedo (a), and optical depth ($\tau$) as determined by IAD using the measured diffuse reflectance ($R_d$), diffuse transmittance ($T_d$), and collimated transmittance ($T_c$) for bovine RPE/choroid. The margin of errors are given below the measured values.

| Wavelength $\lambda$ (nm) | Experimental | | | | | IAD | | | |
|---|---|---|---|---|---|---|---|---|---|
| | $R_d$ | $T_d$ | $T_c$ | a | $\tau$ | $\mu_a$ (cm$^{-1}$) | $\mu_s$ (cm$^{-1}$) | $\mu_t$ (cm$^{-1}$) | $1/\mu_t$ (cm) |
| 514 | 0.1454 ± 0.011 | 0.00050 ± 0.00004 | 0.00030 ± 0.00002 | 0.545 | 8.06 | 245 | 293 | 538 | 0.00186 |
| 501 | 0.1877 ± 0.014 | 0.00050 ± 0.00004 | 0.00040 ± 0.00003 | 0.422 | 7.78 | 300 | 219 | 519 | 0.00193 |
| 488 | 0.0887 ± 0.004 | 0.00060 ± 0.00004 | 0.00050 ± 0.00004 | 0.344 | 7.55 | 330 | 173 | 503 | 0.00199 |
| 476 | 0.1244 ± 0.009 | 0.00140 ± 0.0001 | 0.00100 ± 0.00007 | 0.630 | 7.55 | 238 | 219 | 457 | 0.00219 |

TABLE XIII

The wavelength (λ) dependent diffuse reflectance ($R_d$), diffuse transmittance ($T_d$), determined by the experimental and Monte Carlo techniques for bovine retina.

| Wavelength λ (nm) | Experimental | | Monte Carlo Simulation | | Percent Difference | |
|---|---|---|---|---|---|---|
| | $R_d$ | $T_d$ | $R_d$ | $T_d$ | $R_d$ | $T_d$ |
| 514 | 0.0614 | 0.7862 | 0.0673 | 0.7606 | 8.78 | 3.36 |
| 501 | 0.0598 | 0.7580 | 0.0608 | 0.7404 | 1.57 | 2.38 |
| 488 | 0.0580 | 0.7008 | 0.0539 | 0.6979 | 7.70 | 0.42 |
| 476 | 0.0544 | 0.6531 | 0.0545 | 0.6587 | 0.27 | 0.85 |

TABLE XIV

The wavelength (λ) dependent diffuse reflectance ($R_d$), diffuse transmittance ($T_d$), determined by the experimental and Monte Carlo techniques for bovine RPE/choroid.

| Wavelength λ (nm) | Experimental | | Monte Carlo Simulation | | Percent Difference | |
|---|---|---|---|---|---|---|
| | $R_d$ | $T_d$ | $R_d$ | $T_d$ | $R_d$ | $T_d$ |
| 514 | 0.1454 | 0.00050 | 0.1400 | 0.00053 | 3.89 | 5.03 |
| 501 | 0.1877 | 0.00050 | 0.1728 | 0.00052 | 8.65 | 4.10 |
| 488 | 0.0887 | 0.00060 | 0.0839 | 0.00064 | 5.75 | 6.54 |
| 476 | 0.1244 | 0.00140 | 0.1179 | 0.00150 | 5.52 | 6.95 |

In the retinal tissue, the scattering was found to be significantly higher than the absorption, while in the RPE/choroidal tissue, both the absorption and scattering were found to be comparable. However, the total attenuation coefficients of the RPE/choroid are consistently higher than those of retina. This is believed to be due to the fact that the RPE/choroid is physiologically more opaque and contains melanin. The absorption coefficients of bovine retinal and RPE/choroidal tissues are found to be generally higher than those found in bovine melanin prepared from the bovine RPE melanosomes. This deviation can be attributed to the fact that these tissue are more physiologically intact than the isolated melanin. Owing to the same reason, the total attenuation coefficients of RPE/choroid at all wavelengths investigated are found to be significantly higher than those of retina. Therefore, the penetration depth in RPE/choroid is much smaller than those in retina. The actual values of the absorption and scattering coefficients for the retinal and RPE/choroidal tissues reported in this examples have importance for practical applications requiring the prediction of light transport through pigmented tissue, e.g. in the design of treatment models for laser-induced thermotherapy or photodynamic therapy in the eye, where the degree of pigmentation at the target sites may vary. Variable pigmentation obviously complicates the laser dosimetry for such treatment modes, because the amount of light delivered will have to be adjusted based on the amount of tissue pigmentation in order to achieve some standard clinical effect.

TABLE XV

Polarization shift (in degrees) in the bovine retinal and RPE/choroidal tissues from the left and right eyes.

| Sample Number | Retina | | RPE/Choroid | |
|---|---|---|---|---|
| | Left | Right | Left | Right |
| 1 | 5.96 | 6.96 | 10.92 | 12.16 |
| 2 | 5.92 | 4.92 | 10.00 | 11.94 |
| 3 | 6.94 | 5.00 | 11.96 | 13.92 |
| Average | 6.27 | 5.63 | 10.96 | 12.67 |

TABLE XVI

Polarization shift (in degrees) for the combination of retinal and RPE/choroidal tissues from the bovine left and right eyes.

| Sample Number | Retina | |
|---|---|---|
| | Left | Right |
| 1 | 11.92 | 15.92 |
| 2 | 11.2 | 14.94 |
| 3 | 13.96 | 16.92 |
| Average | 12.36 | 15.93 |

We have also measured the shifts of the polarization in both the retinal and RPE/choroidal tissues taken from the bovine left and right eyes. These data are given in Tables XV and XVI. The experimental data were tested for normality with a statistical software program, SPSS; the data exhibited approximately normal distribution. The observed variations in the polarization shifts between the left and right eyes could be due to the minuscule thickness differences in the prepared tissue samples, particularly, when different spots on the same sample were chosen for collecting the data. Our data clearly suggests that the bovine ocular tissues possess strong polarization properties. However, the RPE/choroidal tissue shows a higher degree of polarization shift than the retina. We have also measured the polarization shifts in the bovine retina at 24 hours of interval and found that the polarization shift decreases significantly after 48 hours after the sample preparation. These values are given in Table XVII. During this period of measurements, the sample was kept refrigerated. The sharp decrease in polarization shift can be attributed to the physiological degradation of the retinal tissue, thereby changing the optical properties drastically.

TABLE XVII

Polarization shift (Δθ) and intensity for healthy human retinal, RPE/choroidal, and retinal and RPE/choroidal tissues combined (in stack).

| Eye | Trial Number | Retina | | RPE/Choroid | | Retina & RPE/Choroid | |
|---|---|---|---|---|---|---|---|
| | | Δθ (degrees) | I (mV) | Δθ (degrees) | I (mV) | Δθ (degrees) | I (mV) |
| Left | 1 | 3.1 | 301 | 7.0 | 318 | 7.8 | 313 |
| | 2 | 3.0 | 309 | 6.5 | 323 | 7.5 | 312 |

TABLE XVII-continued

Polarization shift (Δθ) and intensity for healthy human retinal, RPE/choroidal,
and retinal and RPE/choroidal tissues combined (in stack).

| Eye | Trial Number | Retina | | RPE/Choroid | | Retina & RPE/Choroid | |
|---|---|---|---|---|---|---|---|
| | | Δθ (degrees) | I (mV) | Δθ (degrees) | I (mV) | Δθ (degrees) | I (mV) |
| | 3 | 2.4 | 313 | 6.0 | 329 | 6.8 | 303 |
| | Average | 2.8 ± 0.4 | 307 ± 6 | 6.5 ± 0.5 | 307 ± 6 | 7.3 ± 0.5 | 309 ± 6 |
| Right | 1 | 2.5 | 314 | 6.8 | 322 | 7.3 | 307 |
| | 2 | 2.8 | 310 | 6.5 | 319 | 6.5 | 314 |
| | 3 | 2.0 | 316 | 5.8 | 324 | 6.8 | 316 |
| | Average | 2.4 ± 0.4 | 313 ± 3 | 6.3 ± 0.5 | 307 ± 6 | 6.8 ± 0.4 | 312 ± 5 |

The optical polarization study of ocular tissues is of important significance for optical noninvasive diagnosis of neovascularized tissues. Retinal neovascularization resulting from the diabetic retinopathy is the most common cause of blindness in young patients in major industrialized countries, and choroidal neovascularization resulting from the age-related macular degeneration is the most common cause of severe vision loss in elderly patients. The retinal vascular development occurs by a combination of vasculogenesis and angiogenesis. An additional diagnostic application of retinal polarization is to evaluate the effect of glaucomatous damage to the nerve fiber layer in the retina. The polarization-sensitive optical coherence tomography (PSOCT) can determine retinal nerve fiber layer thickness and birefringence. See Ducros et al. (2001).

High transmittance values in the visible region have been reported in the previous studies on retinal and RPE/choroidal tissues. Geeraets and Berry (1968) found that in the visible region transmittance was greater than 80% in human, rabbit, and monkey retinal tissues. However, Van den Berg and Spekreijse (1997) argued that the data presented by Boettner and Wolter (1962) could be explained only on the basis of pure water content in the ocular tissues. Additional studies on the spectral properties of ocular media ranging from UV through near-infrared have been reported by other authors. The high transmittance and very low reflectance in the visible region reported by these authors are similar to ours.

The polarization studies show that the bovine retina and RPE/choroid possess strong polarization characteristics.

REFERENCES

The following references, to the extent that they provide exemplary procedural or other details supplementary to those set forth herein, are specifically incorporated herein by reference.

Anderson and Parish, *J. Invest. Dermatol.*, 77:13-19, 1981.
Beek et al., *Phys. Med. Biol.*, 42:2255-2261, 1997.
Boettner and Wolter, *Invest. Ophthalmol.*, 1:777-783, 1962.
Campochiaro, *J. Cell. Physiol.*, 184:301-310, 2000.
Chandrasekhar, In: *Radiative Transfer*, Dover, N.Y., 1960.
Delori and Pflibsen, *Appl. Opt.*, 28(6):1061-1077, 1989.
Dryja et al., *Invest. Ophthalmol. Visual Sci.*, 18:231-236, 1979.
Ducros et al., *J. Opt. Soc. Am. A*, 18:2945-2956, 2001.
Ertefai and Profio, *Med. Phys.*, 12:393-400, 1985.
Fowler et al., *Invest. Ophthalmol. Visual Sci.*, 17(6):562-565, 1978.
Geerates and Berry, *Amer. J. Ophthalmol.*, 66:15-20, 1968.
Groenhuis et al., *Appl. Opt.*, 22:2456-2462, 1983.
Hecht, In: *Optics*, 4th ed., Addison Wesley, New York, 2002.
Ishimaru, In: *Wave propagation and scattering in random media*, Vol. 1, Academic Press, New York, 1978.
Kahn and Hiller, *Am. J. Ophthalmol.*, 78:58-67, 1974.
Klein and Klein, In: *Group NDD, Ed. Diabetes in America*. Washington, D.C.: National Institute of Health, 294, 1995.
Knighton et al., *Invest. Ophthalmol. Visual Sci.*, 30(11):2393-2402, 1989.
Kottler, *J. Opt. Soc. Am.*, 50:483-490, 1960.
Kubelka, *J. Opt. Soc. Am.*, 38:448-457, 1948.
Maher, In: *Transmission and absorption coefficients for ocular media of the rhesus monkey*, USAF School of Aerospace Med., Brooks AF Base, TX, Report SAM-TR-78-32, 1978.
McLeod et al., *Invest. Ophthalmol. Visual Sci.*, 37:1322-1333, 1996.
McLeod et al., *Microvasc. Res.*, 33:257-269, 1987.
Mourant et al., *OSA TOPS*, 22:11-14, 1998.
Prahl et al., *Appl. Opt.*, 32:559-568, 1993.
Prahl et al., *SPIE Institute Series*, 5:102-111, 1989.
Prince et al., *J. Clin. Invest.*, 78:295-302, 1978.
Reynolds et al., *Appl. Opt.*, 15:2059-2067, 1978.
Sardar and Levy, 13:106-111, 1998.
Sardar et al., *J. Biomed. Opt.*, 6:404-411, 2001.
Sarna, *J. Photoclem. Photobiol.*, B12:215-258, 1992.
van den Berg and Spekreijse, *Vision Res.*, 37:249-253, 1997.
van Gemert and Star, *Lasers Life Sci.*, 1:287-298, 1987.
van Gemert et al., *Lasers Med. Sci.*, 2:295-302, 1987.
van Gemert et al., *Lasers Surg. Med.*, 5:235-237, 1985.
Vos et al., *J. Opt. Soc. Am.*, 55:573-574, 1965.
Wan et al., *Photochem. Photobiol.*, 34:493-499, 1981.

We claim:

1. A method for diagnosing an ocular disease involving neovascularization, comprising:
   (a) placing an ocular tissue in the path of a first light beam, wherein the ocular tissue comprises retina or RPE/choroidal tissue;
   (b) measuring the maximum intensity of a second light beam that is backscattered from the ocular tissue;
   (c) measuring a polarization shift of the second light beam; and
   (d) diagnosing an ocular disease involving neovascularization if the measured polarization shift corresponds to a polarization shift of polarized light backscattered off of a neovascularized tissue.

2. The method of claim 1, wherein the method is noninvasive.

3. The method of claim 1, wherein the ocular tissue comprises retinal tissue.

4. The method of claim 1, wherein the ocular tissue comprises RPE/choroidal tissue.

5. The method of claim 1, wherein the light beam includes light from a laser.

6. The method of claim 1, wherein the ocular disease includes diabetic retinopathy.

7. The method of claim 1, wherein the ocular disease includes macular degeneration.

8. The method of claim 1, wherein the ocular disease includes cancer.

9. A method for diagnosing an ocular disease involving neovascularization, comprising:
(a) placing an ocular tissue in the path of a first light beam, wherein the ocular tissue comprises retina or RPE/choroidal tissue;
(b) measuring the maximum intensity of a second light beam that is backscattered from the ocular tissue; and
(c) diagnosing an ocular disease involving neovascularization if the measured maximum intensity corresponds to the intensity of a neovascularized tissue.

10. The method of claim 9, wherein the method is noninvasive.

11. The method of claim 9, wherein the ocular tissue comprises retinal tissue.

12. The method of claim 9, wherein the ocular tissue comprises RPE/choroidal tissue.

13. The method of claim 9, wherein the light beam includes light from a laser.

14. The method of claim 9, wherein the ocular disease includes diabetic retinopathy.

15. The method of claim 9, wherein the ocular disease includes macular degeneration.

16. The method of claim 9, wherein the ocular disease includes cancer.

17. A method for diagnosing an ocular disease involving neovascularization, comprising:
(a) placing an ocular tissue in the path of a first light beam, wherein the ocular tissue comprises retina or RPE/choroidal tissue;
(b) aligning an analyzer with the direction of a second light beam that is the most intense light beam backscattered from the ocular tissue;
(c) measuring a polarization shift of the second light beam;
(d) measuring the maximum intensity of the second light beam; and
(e) diagnosing an ocular disease involving neovascularization if the measured polarization shift and maximum intensity correspond to a polarization shift and intensity of a neovascularized tissue.

18. The method of claim 17, wherein the method is noninvasive.

19. An apparatus for diagnosing an ocular disease, comprising:
(a) a laser; a polarizer coupled to the laser;
(b) a tissue sample holder coupled to the polarizer;
(c) an analyzer coupled to the tissue sample holder, wherein the analyzer is configured to be aligned with the direction of the most intense beam backscattered from the tissue;
(d) a detector coupled to the analyzer; and
(e) a data acquisition system coupled to the detector, the data acquisition system configured to measure a polarization shift of a light beam backscattered off of a tissue sample in the holder and diagnose an ocular disease if the measured polarization shift corresponds to a polarization shift of a neovascularized tissue, wherein the data acquisition system includes a computer and the detector.

20. The apparatus of claim 19, wherein the detector includes a photodiode.

21. The apparatus of claim 19, wherein the data acquisition system includes a digital meter.

22. A method for detecting neovascularized tissue, comprising: placing a tissue in the path of a light beam; measuring a polarization shift of the most intense light beam backscattered from the tissue; and detecting neovascularized tissue if the measured polarization shift corresponds to a polarization shift of a neovascularized tissue.

23. The method of claim 22, wherein the method is noninvasive.

24. The method of claim 22, wherein the tissue comprises ocular tissue.

25. The method of claim 24, wherein the ocular tissue comprises retinal tissue.

26. The method of claim 24, wherein the ocular tissue comprises RPE/choroidal tissue.

27. The method of claim 22, wherein the light beam comprises light from a laser.

28. A method for detecting neovascularized tissue, comprising: placing a tissue in the path of a light beam; measuring the maximum intensity of a light beam backscattered from the tissue; and detecting neovascularized tissue if the measured maximum intensity corresponds to the intensity of a neovascularized tissue.

29. The method of claim 28, wherein the method is noninvasive.

30. The method of claim 28, wherein the tissue comprises ocular tissue.

31. The method of claim 30, wherein the ocular tissue comprises retinal tissue.

32. The method of claim 30, wherein the ocular tissue comprises RPE/choroidal tissue.

33. The method of claim 28: wherein the light beam comprises light from a laser.

34. An apparatus for diagnosing an ocular disease, comprising:
(a) a laser;
(b) a polarizer coupled to the laser;
(c) a tissue sample holder coupled to the polarizer, wherein the tissue sample holder is configured to be in the path of a first light beam emitted by the laser;
(d) an analyzer coupled to the tissue sample holder;
(e) a detector coupled to the analyzer, wherein the detector comprises a photodiode; and
(f) a data acquisition system coupled to the detector, the data acquisition system configured to measure the maximum intensity of a second light beam backscattered from a tissue in the tissue sample holder and diagnose an ocular disease if the measured maximum intensity of the second light beam corresponds to an intensity of a neovascularized tissue, wherein the data acquisition system comprises a computer.

35. The apparatus of claim 34, wherein the data acquisition system comprises a digital meter.

36. An apparatus for detecting neovascularized ocular tissue, comprising:
(a) a laser;
(b) a polarizer coupled to the laser;
(c) a tissue sample holder coupled to the polarizer, wherein the tissue sample holder is configured to be in the path of a first light beam emitted by the laser;
(d) an analyzer coupled to the tissue sample holder;

(e) a detector coupled to the analyzer, wherein the detector comprises a photodiode; and (f) a data acquisition system coupled to the detector, the data acquisition system configured to measure a polarization shift of a second light beam backscattered from a tissue in the tissue sample holder and diagnose an ocular disease if the measured polarization shift of the second light beam corresponds to a polarization shift of a neovascularized ocular tissue.

37. An apparatus for detecting neovascularized ocular tissue, comprising:

(a) a laser;

(b) a polarizer coupled to the laser;

(c) a tissue sample holder coupled to the polarizer, wherein the tissue sample holder is configured to be in the path of a first light beam emitted by the laser;

(d) an analyzer coupled to the tissue sample holder;

(e) a detector coupled to the analyzer, wherein the detector comprises a photodiode; and (f) a data acquisition system coupled to the detector, the data acquisition system configured to measure the maximum intensity of a second light beam backscattered from a tissue in the tissue sample holder and diagnose an ocular disease if the measured maximum intensity of the second light beam corresponds to an intensity of a neovascularized ocular tissue.

* * * * *